(12) United States Patent
Gehling et al.

(10) Patent No.: US 8,388,996 B2
(45) Date of Patent: *Mar. 5, 2013

(54) METHODS OF MANUFACTURING A MEDICATED TAMPON ASSEMBLY

(75) Inventors: Steven C. Gehling, Oshkosh, WI (US); Gregory J. Rajala, Neenah, WI (US); James D. Milner, Appleton, WI (US); Dennis S. Everhart, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/205,185

(22) Filed: Aug. 8, 2011

(65) Prior Publication Data

US 2011/0288501 A1 Nov. 24, 2011

Related U.S. Application Data

(63) Continuation of application No. 11/090,554, filed on Mar. 25, 2005, now Pat. No. 7,993,667.

(51) Int. Cl.
*A61F 13/02* (2006.01)
*A61F 9/02* (2006.01)
*A61F 13/20* (2006.01)

(52) U.S. Cl. ........ 424/431; 424/430; 424/433; 514/966; 514/967

(58) Field of Classification Search ................ 424/431, 424/433, 430; 514/966, 967
See application file for complete search history.

(56) References Cited

U.S. PATENT DOCUMENTS

| | | |
|---|---|---|
| 639,864 A | 12/1899 | Von Raitz |
| 706,778 A | 8/1902 | Pond |
| 749,220 A | 1/1904 | Pond |
| 812,768 A | 2/1906 | Pond |
| 812,769 A | 2/1906 | Pond |
| 812,770 A | 2/1906 | Pond |
| 1,234,383 A | 7/1917 | Pond |
| 1,395,295 A | 11/1921 | Pond |
| 1,538,678 A | 5/1925 | Blinn |
| 1,887,526 A | 11/1932 | Spielberg et al. |
| 2,473,368 A | 6/1949 | Flintermann |
| 2,696,456 A | 12/1954 | Hetterick |
| 2,739,593 A | 3/1956 | McLaughlin |
| 2,854,978 A | 10/1958 | Millman et al. |
| 2,922,423 A | 1/1960 | Rickard et al. |
| 3,086,527 A | 4/1963 | Forrest |
| 3,335,726 A | 8/1967 | Maranto |
| 3,415,249 A | 12/1968 | Sperti |
| 3,424,158 A | 1/1969 | Silver |
| 3,499,447 A | 3/1970 | Mattes et al. |
| 3,515,138 A | 6/1970 | Hochstrasser et al. |
| 3,521,637 A | 7/1970 | Waterbury |
| 3,760,808 A | 9/1973 | Bleuer |
| 3,762,414 A | 10/1973 | Burnhill |
| 3,791,385 A | 2/1974 | Davis et al. |
| 3,796,219 A | 3/1974 | Hanke |
| 3,815,600 A | 6/1974 | Groves |
| 3,818,911 A | 6/1974 | Fournier |
| 3,830,237 A | 8/1974 | Bernardin et al. |
| 3,831,605 A | 8/1974 | Fournier |
| 3,884,233 A | 5/1975 | Summey |
| 3,885,564 A | 5/1975 | Groves |
| 3,902,493 A | 9/1975 | Baier et al. |
| 3,916,898 A | 11/1975 | Robinson |
| 3,918,452 A | 11/1975 | Cornfeld |
| 3,921,636 A | 11/1975 | Zaffaroni |
| 3,948,254 A | 4/1976 | Zaffaroni |
| 3,949,752 A | 4/1976 | Van Stee |
| 3,991,760 A | 11/1976 | Drobish et al. |
| 3,993,073 A | 11/1976 | Zaffaroni |
| 3,995,633 A | 12/1976 | Gougeon |
| 3,995,634 A | 12/1976 | Drobish |
| 3,995,636 A | 12/1976 | Murray et al. |
| 4,016,270 A | 4/1977 | Pharriss et al. |
| 4,077,407 A | 3/1978 | Theeuwes et al. |
| 4,077,408 A | 3/1978 | Murray et al. |
| 4,077,409 A | 3/1978 | Murray et al. |
| 4,159,719 A | 7/1979 | Haerr |
| 4,160,020 A | 7/1979 | Ayer et al. |
| 4,160,452 A | 7/1979 | Theeuwes |
| 4,186,742 A | 2/1980 | Donald |
| 4,237,888 A | 12/1980 | Roseman et al. |

(Continued)

FOREIGN PATENT DOCUMENTS

| | | |
|---|---|---|
| DE | 20 24 930 A1 | 12/1971 |
| DE | 21 46 092 A1 | 3/1973 |

(Continued)

OTHER PUBLICATIONS

Nagata, Shunji, "Capsule Technology," *Drug Delivery Technology*, vol. 2, No. 2, Mar./Apr. 2002, printed from Internet web page "www.drugdeliverytech.com." 8 pages.

(Continued)

*Primary Examiner* — Shirley V Gembeh
(74) *Attorney, Agent, or Firm* — Randall W. Fieldhack

(57) ABSTRACT

A method is provided for manufacturing a medicated tampon assembly having a tampon body, the method including applying a formulation including a therapeutic agent to a substrate to produce a plurality of dosage forms; separating one of the dosage forms from the substrate; and coupling one of the dosage forms to the tampon body. A medicated tampon assembly is provided including a dosage form including a formulation including a therapeutic agent; a substrate portion separated from a substrate, wherein the substrate portion is coupled to the dosage form; and a tampon body having a distal end, wherein the substrate portion is coupled to the distal end of the tampon body.

20 Claims, 4 Drawing Sheets

U.S. PATENT DOCUMENTS

| | | |
|---|---|---|
| 4,260,570 A | 4/1981 | Ravel |
| 4,271,835 A | 6/1981 | Conn et al. |
| 4,286,596 A | 9/1981 | Rubinstein |
| 4,291,696 A | 9/1981 | Ring |
| 4,308,867 A | 1/1982 | Roseman et al. |
| 4,309,997 A | 1/1982 | Donald |
| 4,312,348 A | 1/1982 | Friese |
| 4,317,447 A | 3/1982 | Williams |
| 4,318,405 A | 3/1982 | Sneider |
| 4,328,804 A | 5/1982 | Shimatani |
| 4,340,055 A | 7/1982 | Sneider |
| 4,341,211 A | 7/1982 | Kline |
| 4,341,215 A | 7/1982 | Eldridge |
| 4,373,631 A | 2/1983 | Friese et al. |
| 4,383,993 A | 5/1983 | Hussain et al. |
| 4,393,871 A | 7/1983 | Vorhauer et al. |
| 4,402,695 A | 9/1983 | Wong |
| 4,405,323 A | 9/1983 | Auerbach |
| 4,421,504 A | 12/1983 | Kline |
| 4,424,054 A | 1/1984 | Conn et al. |
| 4,439,194 A | 3/1984 | Harwood et al. |
| 4,483,846 A | 11/1984 | Koide et al. |
| 4,551,148 A | 11/1985 | Riley, Jr. et al. |
| 4,553,965 A | 11/1985 | Conn et al. |
| 4,560,549 A | 12/1985 | Ritchey |
| 4,582,717 A | 4/1986 | Von Bittera et al. |
| 4,601,714 A | 7/1986 | Burnhill |
| 4,610,659 A | 9/1986 | Friese |
| 4,649,075 A | 3/1987 | Jost |
| 4,690,671 A | 9/1987 | Coleman et al. |
| 4,693,705 A | 9/1987 | Gero |
| 4,795,422 A | 1/1989 | Conner et al. |
| 4,857,044 A | 8/1989 | Lennon |
| 4,871,542 A | 10/1989 | Vilhardt |
| 4,922,928 A | 5/1990 | Burnhill |
| 4,923,440 A | 5/1990 | Genaro |
| 4,979,947 A | 12/1990 | Berman |
| 4,983,393 A | 1/1991 | Cohen et al. |
| 5,002,540 A | 3/1991 | Brodman et al. |
| 5,041,080 A | 8/1991 | Shimatani et al. |
| 5,045,058 A | 9/1991 | Demetrakopoulos |
| 5,069,906 A | 12/1991 | Cohen et al. |
| 5,070,889 A | 12/1991 | Leveen et al. |
| 5,084,277 A | 1/1992 | Greco et al. |
| 5,116,619 A | 5/1992 | Greco et al. |
| 5,201,326 A | 4/1993 | Kubicki et al. |
| 5,213,566 A | 5/1993 | Weissenburger |
| 5,273,521 A | 12/1993 | Peiler et al. |
| 5,295,984 A | 3/1994 | Contente et al. |
| 5,299,581 A | 4/1994 | Donnell et al. |
| 5,330,427 A | 7/1994 | Weissenburger |
| 5,330,761 A | 7/1994 | Baichwal |
| 5,362,498 A | 11/1994 | Aiache |
| 5,383,891 A | 1/1995 | Walker |
| 5,393,528 A | 2/1995 | Staab |
| 5,417,224 A | 5/1995 | Petrus et al. |
| 5,466,463 A | 11/1995 | Ford |
| 5,527,534 A | 6/1996 | Myhling |
| 5,529,782 A | 6/1996 | Staab |
| 5,542,914 A | 8/1996 | Van Iten |
| 5,612,051 A | 3/1997 | Yue |
| 5,646,206 A | 7/1997 | Coffin et al. |
| 5,676,647 A | 10/1997 | Cimber |
| 5,683,358 A | 11/1997 | Nielsen et al. |
| 5,693,009 A | 12/1997 | Fox et al. |
| 5,769,813 A | 6/1998 | Peiler et al. |
| 5,788,980 A | 8/1998 | Nabahi |
| 5,840,055 A | 11/1998 | Sgro |
| 5,912,006 A | 6/1999 | Bockow et al. |
| 5,958,461 A | 9/1999 | Larsen |
| 5,988,386 A | 11/1999 | Morrow |
| 5,993,856 A | 11/1999 | Ragavan et al. |
| 6,036,666 A | 3/2000 | Peiler et al. |
| 6,039,968 A | 3/2000 | Nabahi |
| 6,086,909 A | 7/2000 | Harrison et al. |
| 6,095,999 A | 8/2000 | Jackson et al. |
| 6,096,332 A | 8/2000 | Yang |
| 6,103,256 A | 8/2000 | Nabahi |
| 6,126,959 A | 10/2000 | Levine et al. |
| 6,197,327 B1 | 3/2001 | Harrison et al. |
| 6,200,288 B1 | 3/2001 | Heaton et al. |
| 6,203,514 B1 | 3/2001 | Clifford |
| 6,264,638 B1 | 7/2001 | Contente |
| 6,264,972 B1 | 7/2001 | Drury |
| 6,316,019 B1 | 11/2001 | Yang |
| 6,328,991 B1 | 12/2001 | Myhling |
| 6,416,778 B1 | 7/2002 | Ragavan et al. |
| 6,416,779 B1 | 7/2002 | D'Augustine et al. |
| 6,524,269 B2 | 2/2003 | McNamara |
| 6,526,980 B1 | 3/2003 | Tracy et al. |
| 6,558,362 B1 | 5/2003 | Chaffringeon |
| 6,582,389 B2 | 6/2003 | Buzot |
| 6,592,540 B2 | 7/2003 | Decarlo |
| 6,888,043 B2 | 5/2005 | Geiser et al. |
| 6,899,700 B2 * | 5/2005 | Gehling et al. ............. 604/285 |
| 6,958,057 B2 | 10/2005 | Berg, Jr. et al. |
| 7,331,937 B2 | 2/2008 | Arnould |
| 7,708,726 B2 | 5/2010 | Hayes et al. |
| 2002/0161088 A1 | 10/2002 | Kochvar et al. |
| 2002/0193726 A1 | 12/2002 | Cimber |
| 2003/0028177 A1 | 2/2003 | Berg et al. |
| 2003/0045829 A1 | 3/2003 | Gehling et al. |
| 2003/0120224 A1 * | 6/2003 | Geiser et al. ............. 604/285 |
| 2003/0139709 A1 | 7/2003 | Gehling |
| 2003/0144639 A1 | 7/2003 | Gehling |
| 2003/0207019 A1 | 11/2003 | Shekalim et al. |
| 2004/0043061 A1 | 3/2004 | Leon et al. |
| 2004/0224008 A1 | 11/2004 | Zhang |
| 2006/0069341 A1 | 3/2006 | Bichsel et al. |
| 2006/0100566 A1 | 5/2006 | Zbella et al. |
| 2006/0213918 A1 | 9/2006 | Rajala et al. |
| 2006/0213919 A1 | 9/2006 | Heuer et al. |
| 2006/0217652 A1 | 9/2006 | Heuer et al. |
| 2007/0128254 A1 | 6/2007 | Heuer et al. |
| 2007/0141118 A1 | 6/2007 | Damico et al. |

FOREIGN PATENT DOCUMENTS

| | | |
|---|---|---|
| DE | 2 309 575 A | 9/1974 |
| DE | 32 48 152 A1 | 6/1984 |
| EP | 0 110 793 B1 | 3/1987 |
| EP | 0 747 045 A2 | 12/1996 |
| EP | 0 962 201 A1 | 12/1999 |
| GB | 2 277 447 A | 11/1994 |
| JP | 02-212431 A | 8/1990 |
| JP | 07-000450 A | 1/1995 |
| WO | WO 79/00014 A1 | 1/1979 |
| WO | WO 82/02489 A1 | 8/1982 |
| WO | WO 82/04185 A1 | 12/1982 |
| WO | WO 87/02576 A1 | 5/1987 |
| WO | WO 94/08536 A1 | 4/1994 |
| WO | WO 97/19680 A1 | 6/1997 |
| WO | WO 97/45066 A1 | 12/1997 |
| WO | WO 99/47121 A1 | 9/1999 |
| WO | WO 99/48453 A1 | 9/1999 |
| WO | WO 00/66213 A1 | 11/2000 |
| WO | WO 01/13836 A1 | 3/2001 |
| WO | WO 01/80937 A1 | 11/2001 |
| WO | WO 02/03896 A1 | 1/2002 |
| WO | WO 02/09631 A1 | 2/2002 |
| WO | WO 02/051718 A1 | 7/2002 |
| WO | WO 03/007862 A2 | 1/2003 |
| WO | WO 03/020240 A2 | 3/2003 |
| WO | WO 03/037381 A1 | 5/2003 |
| WO | WO 03/059318 A2 | 7/2003 |
| WO | WO 06/104631 A1 | 10/2006 |

OTHER PUBLICATIONS

Patent Abstracts of Australia AU-A-32971/95: Description of Trevor William Lucas, "Herbal Tampon.", 2001.

Derwent World Patent Database abstract of ZA 87/9748 A: Description of D. Eyal, "Tampon.", Feb. 15, 2000.

* cited by examiner

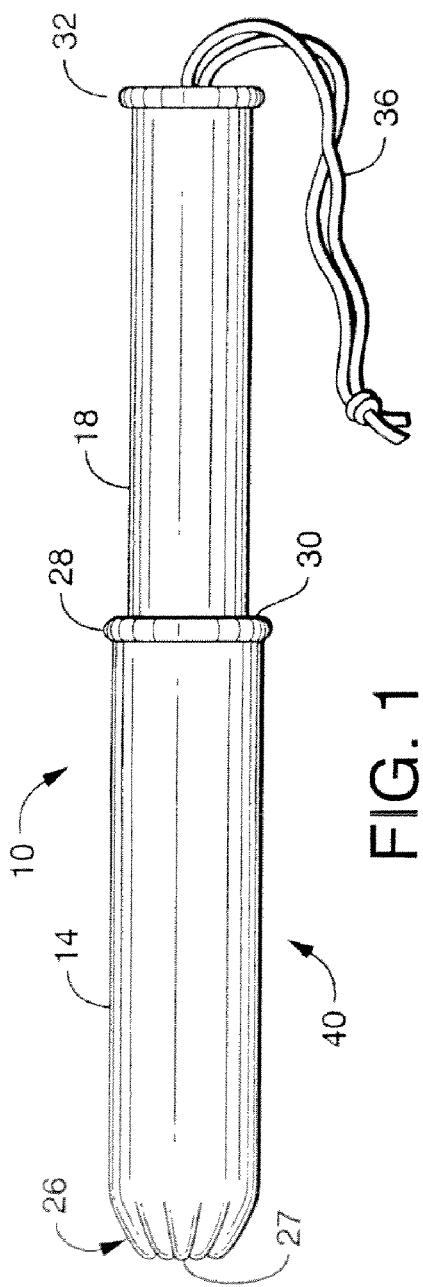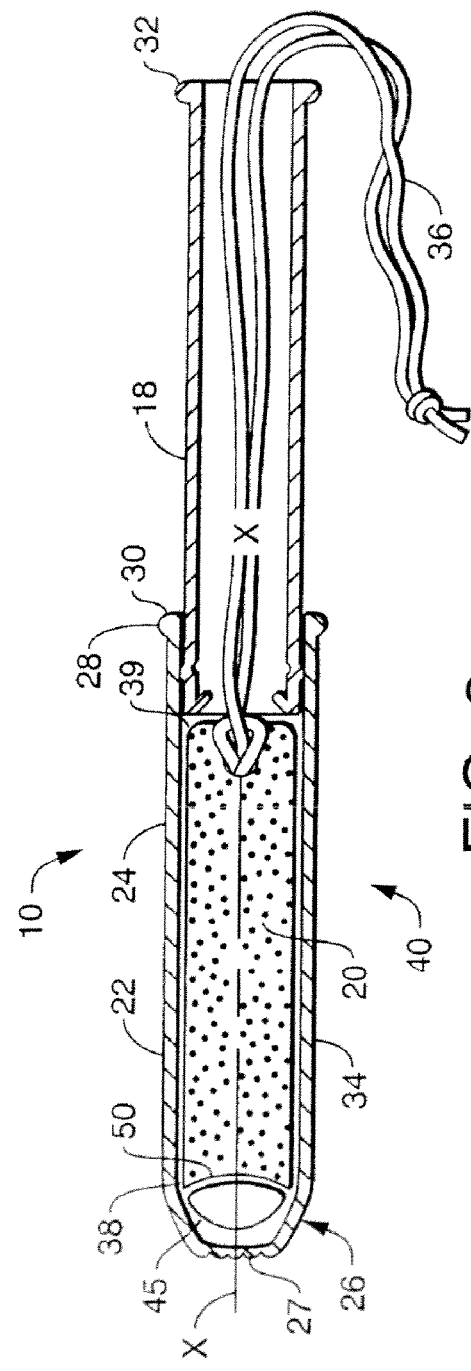

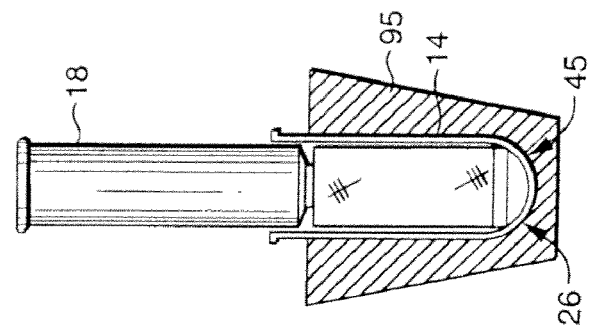
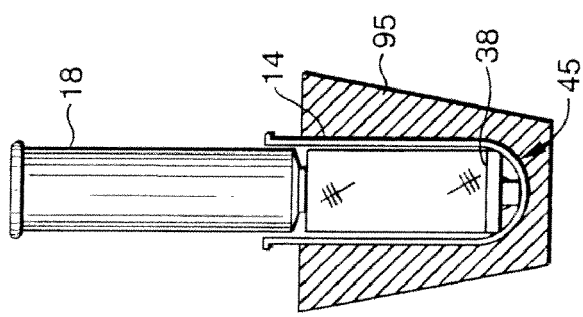
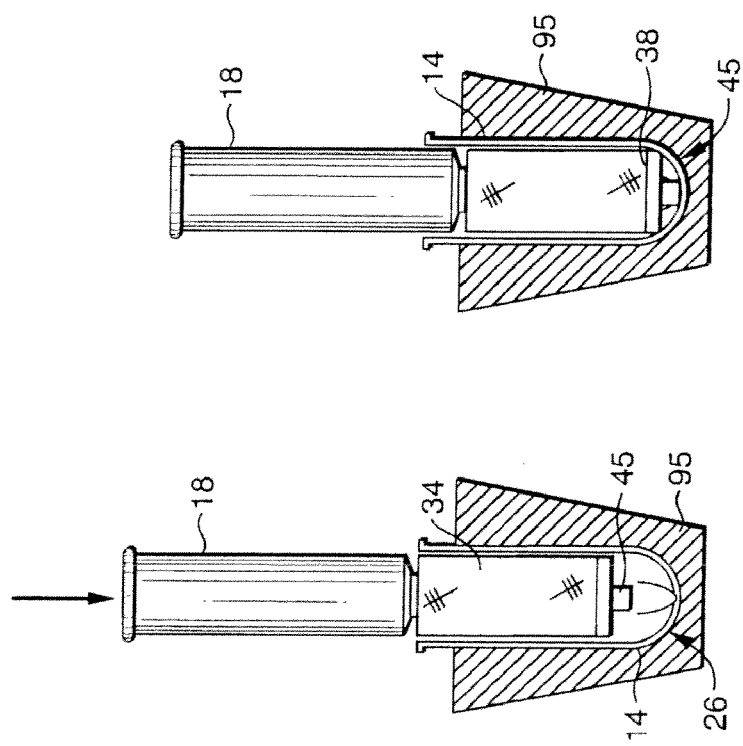
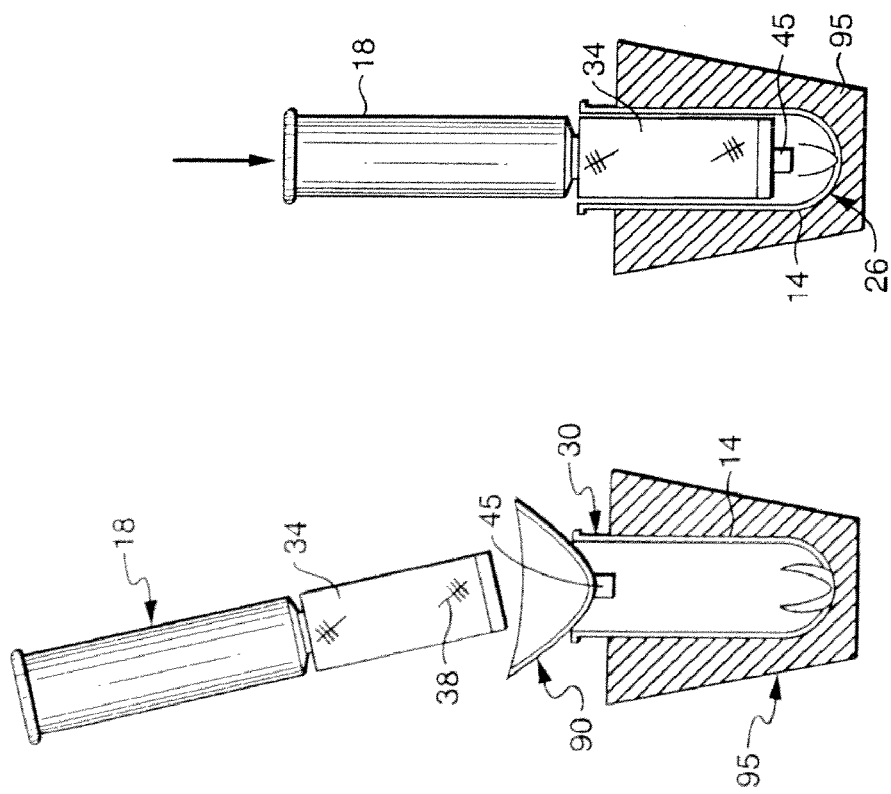

METHODS OF MANUFACTURING A MEDICATED TAMPON ASSEMBLY

This application claims priority as a continuation of application Ser. No. 11/090,554, filed on filed on Mar. 25, 2005 now U.S. Pat. No. 7,993,667. The entirety of application Ser. No. 11/090,554 is incorporated herein by reference.

BACKGROUND

This invention pertains to methods of manufacturing medicated tampon assemblies used for the application of various therapeutic treatments or preparations into the vaginal or other cavity.

Many disease states and physiological conditions may occur in a woman, including symptoms associated with pre-menstrual syndrome, menstruation, and menopause. These symptoms may include dysmenorrhea (menstrual cramping), irritability, water retention, moodiness, depression, anxiety, skin changes, headaches, breast tenderness, tension, weight gain, cravings, fatigue hot flashes, itching, and other associated sensory maladies.

Many of these symptoms are due to changes in hormonal levels throughout the menstrual cycle. One example that affects a large number of post-pubescent women is dysmenorrhea, which is the occurrence of painful uterine cramps during menstruation. Menstrual cramping is associated with increased levels of prostaglandin F2$\alpha$, prostaglandin E2, and, in some cases, leukotrienes in the endometrium and menstrual fluid. These eicosinoids lead to restricted blood flow to the uterus and increased uterine contractions, causing pain.

Various analgesics may be effective in limiting the pain from dysmenorrhea; however some orally-delivered analgesics can cause nausea and vomiting or other untoward side effects; therefore alternative routes of analgesic delivery are of interest.

Attempts have been made to deliver analgesics in the vicinity of the cervix and the vaginal mucosa using various vaginally-inserted devices and methods. Because many of these symptoms typically occur in conjunction with menstruation, some have tried to combine an analgesic with a tampon by coating the tampon, dipping the tampon, or by combining the analgesic with the tampon materials.

For example, in a method of preparation of such a product appropriate for a laboratory setting, a formulation of a fatty compound excipient and an analgesic are heated to a liquid state. Constant mixing of the heated formulation is required to produce a homogeneous formulation. The formulation is then poured onto the tip of a tampon held in a form to contain the liquid. As the formulation cools, the ingredients solidify into a solid waxy substance that has adhered to the absorbent material of the tampon and is thereby securely fastened to the tip of the tampon.

SUMMARY OF THE INVENTION

Several problems are inherent in a process that attempts to introduce a formulation including a therapeutic agent into or onto a tampon by coating, dipping, solidifying, or the like. Processes such as these may work in a laboratory setting but may not be feasible within an automated tampon manufacturing process. Because of dosing requirements, the formulation including a therapeutic agent must be maintained in a solution that is both homogeneous and of the proper purity to ensure consistent concentration of the therapeutic agent. These requirements are difficult to accomplish during production operation of an automated tampon manufacturing process, and are significantly more difficult to maintain when the automated tampon manufacturing process stops. In addition, different styles and sizes of tampons may have different densities and will absorb an applied liquid formulation including a therapeutic agent differently, resulting in variability in therapeutic agent concentrations across such different tampons.

Specifically, the need to provide constant agitation or mixing of the formulation including a therapeutic agent poses challenges as to how to keep a therapeutic agent homogeneously suspended in a solution when the automated tampon manufacturing process stops. The use of inline mixers and recirculation of the heated liquid formulation during machine stops may provide a method to keep the formulation moving and mixed. However, because a machine could be stopped for several hours, the stability of some formulation mixtures may be compromised by long durations at elevated temperatures, or by mechanical shear forces due to the continuous pumping of the recirculating liquid.

The present invention solves these problems by coupling a dosage form to a tampon to form a medicated tampon assembly. The dosage form, which includes a therapeutic agent, is solid or semi-solid at room temperature, is sufficiently stable, and may be manufactured separately in a controlled facility, whereby dose is easily controlled through controls on concentration and purity.

More specifically, the present invention relates to a method for manufacturing a medicated tampon assembly having a tampon body, the method including applying a drug formulation including a therapeutic agent to a substrate to produce a plurality of dosage forms; separating one of the dosage forms from the substrate; and coupling one of the dosage forms to the tampon body.

In another aspect, the present invention provides a medicated tampon assembly including a dosage form including a formulation including a therapeutic agent; a substrate portion separated from a substrate, wherein the substrate portion is coupled to the dosage form; and a tampon body having a distal end, wherein the substrate portion is coupled to the distal end of the tampon body.

The advantages of using a pre-manufactured dosage form over an in-line process where the medicated ingredients are applied to the tampon coincident with the tampon manufacturing process are numerous. The dosage form would be desirably produced at a pharmaceutical manufacturer whose manufacturing facility meets current regulatory and quality requirements for drugs and/or devices as appropriate. This could ensure that a therapeutic agent with the correct dose and purity is dispersed within the dosage form. The use of separately-manufactured dosage forms simplifies the modifications to an existing tampon manufacturing process. The use of separately-manufactured dosage forms allows multiple types of therapeutic agents to be applied to the tampon. The chemical and physical stabilities of the dosage form are not compromised by the assembly process onto the tampon. The process is less dependent on the physical characteristics of the absorbent structure of the tampon, because only a partial phase change of the dosage form may be required to bond with the tampon.

The present invention relates to a dosage form that is integral with or associated with a feminine care product. The dosage form including the therapeutic agent and excipients may include any therapeutic agent that may be absorbed into the body through the vaginal or other epithelium, or deposited topically on the vaginal or other epithelium, for the purposes of treating a physiological disease, state, or condition.

Other objects and advantages of the present invention will become more apparent to those skilled in the art in view of the following description and the accompanying drawings.

BRIEF DESCRIPTION OF THE DRAWINGS

FIG. 1 is a view of a two-piece tampon assembly to be used in conjunction with a medicated tampon assembly.

FIG. 2 is a cross-sectional view of the tampon assembly shown in FIG. 1.

FIG. 6 is a schematic cross-sectional view of one method of manufacturing the medicated tampon assembly of FIG. 2.

DETAILED DESCRIPTION OF THE PREFERRED EMBODIMENTS

Figure 4:
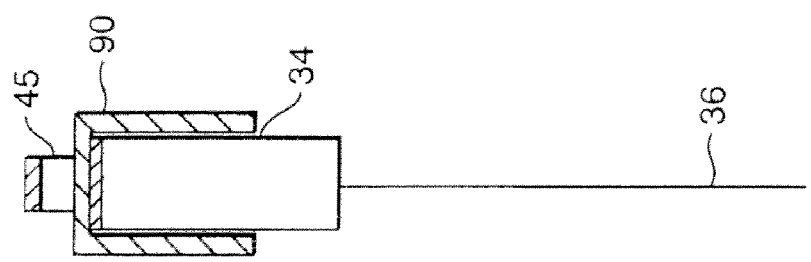
FIG. 4 is a simplified schematic view showing key features of the medicated tampon assembly of FIG. 2.

The invention as described herein will be described for exemplary purposes using a tampon as an example of a feminine care product. The invention, however, applies equally to other forms of products, including tampon-like devices and vaginally-inserted devices, and should not be limited to the example described herein. In addition, although the example described includes a tampon with absorbent material, a product without absorbent material, such as a tampon applicator or other similar applicator, is also contemplated within the invention. Also contemplated is the use of the invention described herein in conjunction with non-catamenial feminine products such as incontinence products, including female incontinence inserts.

The term "surface" and its plural generally refer herein to the outer or the topmost boundary of an object.

The term "dosage form" is used herein as a generic term for a unit form including a formulation that includes a therapeutic agent. The dosage form includes a discrete and consistent quantity of the therapeutic agent to allow for consistent dosing of one receiving the dosage form. The dosage form may be a suppository, a capsule, or any other suitable form. The dosage form may also be spherical, ovoid, domal, generally flat, or any other suitable shape dictated by the needs of the application of the dosage form. The dosage form may have convex, concave, planar, arcuate, or any other suitable surfaces as dictated by the needs of the application of the dosage form.

FIGS. 1-2 illustrate a delivery device in the form of a medicated tampon assembly 10, including a first member 14 and a second member 18, which is designed to house a tampon 20 and provide a comfortable means of inserting the tampon 20 into a woman's vagina.

The first member 14 of the medicated tampon assembly 10 may be in the form of a spirally wound, convolutely wound or longitudinally seamed hollow tube which is formed from paper, paperboard, cardboard, plastic, other suitable material, or a combination of such materials. Any plastic in the first member 14 is preferably polyethylene, but may be polypropylene or other suitable plastic. The first member 14, also commonly referred to as an outer tube, may be of any suitable dimensions necessary to house a particular size of tampon 20. The first member 14 has a wall 22 with an outside or exterior surface 24.

The first member 14 is sized and configured to house the tampon 20, and should have a substantially smooth exterior surface 24 which will facilitate insertion of the first member 14 into a woman's vagina. When the exterior surface 24 is smooth and/or slippery, the first member 14 will easily slide into a woman's vagina without subjecting the internal tissues of the vagina to abrasion. The first member 14 may be coated to give it a high slip characteristic. Wax, polyethylene, a combination of wax and polyethylene, cellophane and clay are representative coatings that may be applied to the first member 14 to facilitate comfortable insertion. The first member 14 itself may be formulated to give it a high slip characteristic, including the addition of additives to the resin from which the first member is made, or by an alteration in physical structure of the exterior surface 24, such as adding pebbling or other bumps, to decrease the amount of surface area in contact with the vaginal or other epithelium.

Referring to FIG. 1, an insertion tip 26 is shown having a plurality petals 27 that may radially open such that the insertion tip 26 has a diameter approximately equal to or greater than the diameter of the first member 14. The petals 27 may be either even or odd in number and may be equally spaced apart or non-uniformly arranged. In another aspect, the insertion tip 26 may be provided without petals 27.

The first member 14 may have a fingergrip ring 28 located proximate the receiving end 30. The fingergrip ring 28 provides an enlarged surface onto which one or more fingers of the user may rest.

As stated above, the medicated tampon assembly 10 includes a second member 18, also commonly referred to as an inner tube. The second member 18, like the first member 14, may be a spirally wound, a convolutely wound or a longitudinally seamed hollow tube constructed from paper, paperboard, cardboard, plastic, other suitable material, or a combination thereof. The second member 18 may be constructed of the same material as the first member 14 or it may be made out of a different material. The second member 18 may also be a solid stick or use some other unique shape. It is also possible to form a finger flange 32 on the free end 31 of the second member 18 to provide an enlarged surface onto which the user's forefinger may rest. The finger flange 32 thereby functions as a seat for the forefinger and facilitates movement of the second member 18 into the first member 14.

In an alternate aspect of the present invention (not shown), the first member 14 and second member 18 together may be replaced by a stick applicator. The stick applicator is used to insert the tampon 20, after which the stick applicator is withdrawn.

A tampon 20 may be an absorbent member primarily designed to be worn by a woman during her menstrual period to absorb menses and other body fluids. The tampon 20 includes a tampon body 34 and a withdrawal string 36. The tampon body 34 is normally compressed into the form of a cylinder and may have a blunt, rounded or shaped forward end. The tampon body 34 has a forward or distal end 38 that is closer to the cervix when the tampon 20 is in use. The tampon body 34 also has a proximal end 39 that is closer to the vaginal opening when the tampon 20 is in use. The tampon 20 commonly has a withdrawal string 36 fastened to the tampon body 34 and extending from the proximal end 39. The withdrawal string 36 serves as a means for withdrawing the tampon 20 from the woman's vagina. Catamenial tampons suitable for use in the present invention include any absorbent material as is known in the art. The tampon body 34 may be formed into specific shapes such as various cup shapes to enhance the therapeutic agent contact area with the cervix, posterior fornix, anterior fornix, lateral fornices, vaginal epithelium areas, or conformance to other anatomical areas within the vaginal or other cavity.

A medicated tampon assembly 10 includes the tampon 20 and also includes a therapeutic agent included in a dosage form 45. For the purposes of this invention, any therapeutic agent that will treat the vaginal or other cavity or will be absorbed into a user's body through the vaginal or other epithelium for the purposes of treating diseases or conditions, promoting the growth of normal vaginal flora, or promoting vaginal health may be used. Examples of therapeutic agents that may be used include, but are not limited to, botanicals, vitamins, moisturizers, antifungal agents, antibacterial agents, pro-biotic agents, calcium, magnesium, hormones, analgesics, prostaglandin inhibitors, prostaglandin synthetase inhibitors, leukotriene receptor antagonists, essential fatty acids, sterols, anti-inflammatory agents, vasodilators, chemotherapeutic agents, and agents to treat infertility.

Some therapeutic agents for use in this invention are absorbable through the vaginal epithelium and travel to the uterus by a unique portal of veins and arteries that are known to exist between the vagina, the cervix, and the uterus. This anastomosis eliminates first-pass metabolism by the liver, effectively delivering higher concentrations of the therapeutic agent to the uterus than would otherwise be available via oral dosing. Those of skill in the art know the efficacy of various therapeutic agents when introduced at a particular anatomical location. For example, when the therapeutic agent is selected to treat dysmenorrhea, it preferably is selected from the following group: nonsteroidal anti-inflammatory drugs (NSAIDs), prostaglandin inhibitors, COX-2 inhibitors, local anesthetics, calcium channel blockers, potassium channel blockers, β-adrenergic agonists, leukotriene blocking agents, smooth muscle inhibitors, and drugs capable of inhibiting dyskinetic muscle contraction.

Alternatively, therapeutic agents modify the vaginal or other environment to enhance the wellness of this anatomical region. The benefits may be rather basic, for example increasing comfort by providing moisturization and/or lubricity. These benefits may also be more complex, for example modulating epithelial cell function to address vaginal atrophy. The beneficial therapeutic agents may reduce negative sensations such as stinging, burning, itching, etc, or introduce positive sensations to improve comfort.

In one aspect of the present invention, the dosage form 45 may be produced in any suitable form including, but not limited to, tablets, capsules, suppositories, gels, disks, lozenges, films, coatings, and other forms. In an alternate aspect of the present invention, the dosage form 45 may be produced in an encapsulated form.

In another aspect of the present invention, the dosage form 45 may be designed to melt at approximately body temperature, or to dissolve or otherwise disperse in the presence of a sufficient aqueous or other liquid trigger, or appropriate chemistry, such as a suitable pH. The dosage form 45 may be in any suitable form including, but not limited to, tablets, capsules, suppositories, disks, lozenges, films, coatings, and other forms.

Additionally, the dosage form 45 may be formed in any shape to promote attachment to the distal end 38 of the tampon body 34 and/or to promote contact with anatomical structures such as the vaginal epithelium, the posterior fornix, the anterior fornix, the lateral fornices, the cervix, or other structures.

The dosage form 45 may include any therapeutic agent, excipient, formulation, compound, or combination thereof that is desirable to introduce into the vaginal or other cavity, including excipients to promote the functionality of the therapeutic agent. The excipients may assist the release of the therapeutic agent, or assist in the absorbency of the therapeutic agent into the vaginal or other epithelium. The use of excipients to facilitate the formulation, delivery, stability, and aesthetic properties of a therapeutic agent delivery system is well known to those familiar with the art.

Examples of materials that may accompany the therapeutic agent in the dosage form 45 include excipients, biologically-compatible adhesives, surfactants, and penetration enhancers. An example of a suitable excipient is SUPPOCIRE suppository base, available from Gattefossé Corp. SUPPOCIRE suppository base is a semi-synthetic glyceride. An example of a suitable biologically-compatible adhesive is hydroxypropyl methylcellulose (HPMC), available as METHOCEL*K15M from The Dow Chemical Company. An example of a suitable surfactant is polysorbate 80, available from Spectrum Chemical Manufacturing Corp. An example of a suitable penetration enhancer is LABRAFIL M 1944 C nonionic amphiphilic excipient, available from Gattefossé Corp.

The dosage form 45 may be combined with any absorbent tampon design. The dosage form 45 is preferably positioned at the distal end 38 of the tampon body 34. In alternate aspects of the present invention, the dosage form 45 may be positioned at the proximal or string end 39 of the tampon body 34, or any other suitable position between the distal and proximal ends 38, 39 of the tampon body 34. The dosage form 45 may be designed to partially or fully cover the distal end 38 of the tampon body 34. The tampon body 34 may be formed into specific shapes such as various cup shapes to enhance the therapeutic agent contact area with the cervix, posterior fornix, vaginal or other epithelium areas, or conformance to other anatomical areas within the vaginal or other cavity.

In other various aspects of the present invention, the tampon 20 may include a recess, a dimple, a depression, a concavity, or a reservoir (generically a recess) 50 at the distal end 38 (see FIG. 2), at the proximal end 39, or at any point between the distal and proximal ends 38, 39. The recess 50 is designed to accommodate the dosage form 45. The dosage form 45 may be applied to the recess 50 by any method described herein or by any other suitable method. In an alternate aspect of the present invention, the recess 50 may be formed as a simple dimple. In other alternate aspects of the present invention, the distal end 38 of the tampon 20 may flat, convex, or of any other suitable shape or arrangement.

The dosage form 45 may be produced by the same manufacturer as the manufacturer of the tampon assembly 40. The dosage form 45 may also be produced by a separate manufacturer and provided to the tampon manufacturer in any suitable manner. As an example, a dosage form manufacturer with a facility specifically designed for pharmaceutical manufacturing under cGMP, FDA, or other regulatory requirements may produce the dosage forms 45 under conditions such that homogeneity, concentration, and purity of the dosage form 45 are closely controlled, and such that production is in accordance with applicable regulations. The dosage form 45 may then be sealed and shipped to the manufacturer of the tampon assembly 40. In this manner, the dosage form 45 is produced by a manufacturer with appropriate experience, and the tampon manufacturer may be relieved of establishing a pharmaceutical-production facility.

Figure 3:
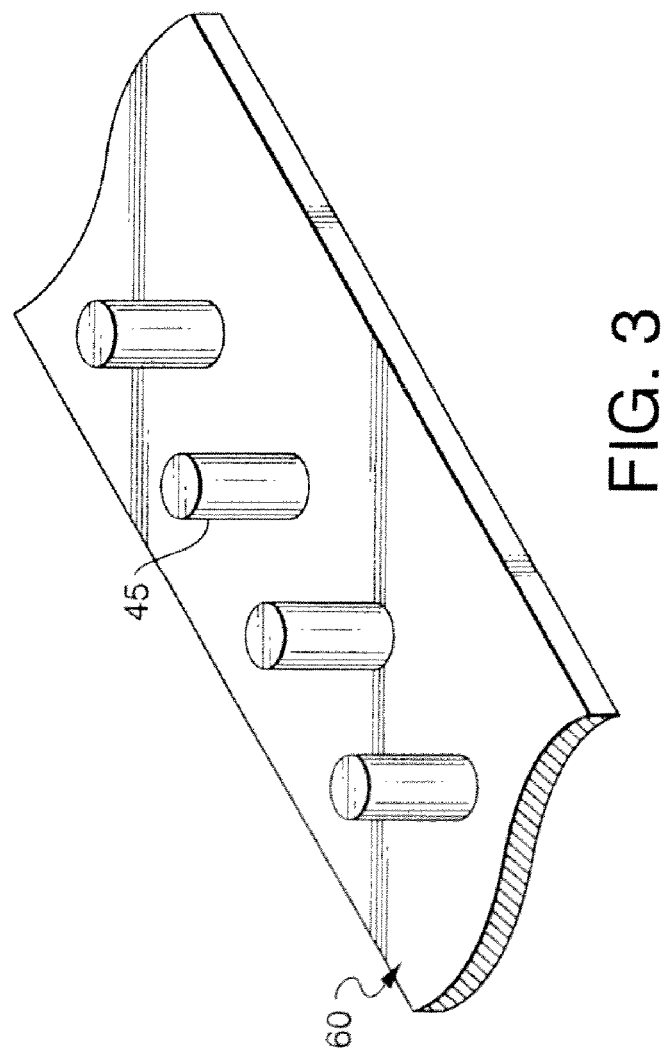
FIG. 3 is a perspective view of a portion of a substrate carrying dosage forms to be used in conjunction with the medicated tampon assembly of FIG. 2.

The dosage form 45 may be produced by applying the formulation including a therapeutic agent to a substrate 60 (see FIG. 3). The substrate 60 may be a film or any other generally planar material including paper products. The substrate 60 may be meltable, dissolvable, or chemically reactive. The material of the film may be similar or substantially identical to the material of the dosage form 45, but may have properties differentiated from the material of the dosage form 45. Examples of suitable films include dissolvable films made from poly-vinyl alcohol, mixtures of pectin and poly-vinyl alcohol, gelatin, and HPMC. These and other suitable materials are described in U.S. Pat. No. 5,646,206 to Coffin et al. and entitled "Films Fabricated From Mixtures Of Pectin And Poly(Vinyl Alcohol)," U.S. Pat. No. 5,529,782 to Staab and entitled "Dissolvable Device For Contraception Or Delivery Of Medication," US Patent Application No. 2004/0224008 A1 entitled "Dissolvable Backing Layer For Use With A Transmucosal Delivery Device," US Patent Application No. 2004/0043061 A1 to Leon et al. and entitled "Dissolvable Films Comprising Suspended Non-Soluble Pharmaceutically Active Ingredients, Apparatus And Methods For Their Manufacture And Use," US Patent Application No. 2002/0161088 A1 to Cochvar et al. and entitled "Rapidly Dissolvable Polymer Films And Articles Made Therefrom," and Nagata, Shunji, "Advantages to HPMC Capsules: A New Generation's Hard Capsule," Drug Delivery Technology, March/April 2002, Vol. 2, No. 2, available at Internet site www-.drugdeliverytech.com.

Many suitable materials, including an excipient, may be used to form the substrate 60. As an example of an excipient material with desired properties, SUPPOCIRE suppository base or other semi-synthetic glyceride is available in different compounds having different melt properties. SUPPOCIRE suppository base or other semi-synthetic glyceride may be used as a significant excipient component of the dosage form, as well as the primary component of the substrate 60.

In various aspects of the present invention, the substrate 60 may be durable or semi-durable, and materials in the substrate 60 may include plastics, cellulose, metals such as aluminum, thermo-formed films, MYLAR film or MYLAR film composites, or other suitable or pharmaceutical-grade materials.

In a different aspect of the present invention, the substrate 60 may be formed with dimples, pockets, or other suitable recesses. The formulation including a therapeutic agent, when applied to the substrate 60, will fill the recess and take on the shape of the recess. The recess is thus shaped to create the desired shape of the dosage form. The substrate 60 may be in the form of a sheet, a strip, or any suitable form. Once the recesses of the substrate 60 are filled with the formulation including a therapeutic agent, the substrate 60 may be rolled, stacked, or otherwise packaged as appropriate and shipped and/or further processed. The substrate 60 may be fed into a machine process where the dosage forms may be removed from the substrate 60 by cutting, dumping, a pick and place mechanism, or any other suitable method.

The dosage form 45 may be produced by applying a metered amount of the formulation including a therapeutic agent to the substrate. The formulation including a therapeutic agent may be applied to the substrate 60 by inkjet printing or by any other suitable printing method. The formulation including a therapeutic agent may also be applied to the substrate 60 by depositing a metered amount of the formulation including a therapeutic agent onto the substrate 60 using any suitable equipment, including a positive-displacement pump. Any other suitable method of applying the formulation including a therapeutic agent to the substrate 60 may be used. In addition, more than one layer of therapeutic agent or other material may be applied to the substrate 60 by any of these methods. Any number of applications may be made to the same substrate 60. If the substrate 60 is a strip, the formulation including a therapeutic agent may be applied sequentially to create a series of dosage forms 45 on the substrate 60. Such series of dosage forms 45 may be arrayed on the substrate 60 in either a one- or two-dimensional array. The substrate 60 may then be fed into a machine process to be automatically merged with a series of tampon bodies 34, as described below.

Once the formulation including a therapeutic agent is applied to the substrate 60 to create a plurality of dosage forms 45, the substrate 60 may be cut to create individual dosage forms 45. This cutting may be performed by die-cutting or any other suitable method. The dosage forms 45 may also be removed from the substrate 60, leaving the substrate 60 intact.

Figure 5:
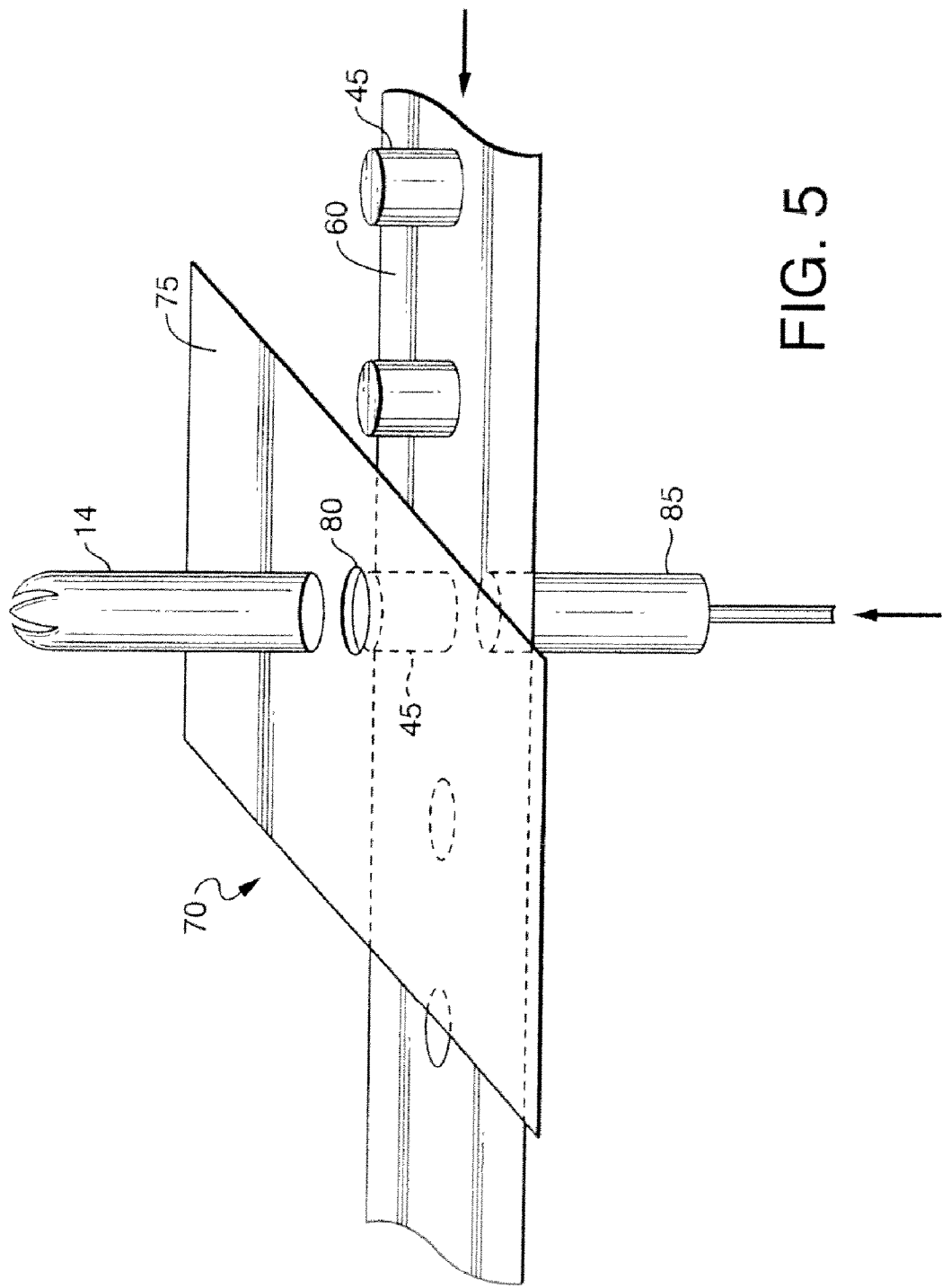
FIG. 5 is a schematic view illustrating the mechanism for die-cutting a substrate carrying dosage forms.

Referring to FIG. 5, in one aspect of the present invention, the substrate 60 carrying the dosage forms 45 may be fed into a machine process. For example, a substrate 60 in the form of a strip carrying a plurality of dosage forms 45 may be passed along a die 70 including at least one plate 75 containing an aperture 80, where the plate 75 and aperture 80 define a plane. The plate 75 may be oriented vertically, horizontally, or in any other suitable orientation. If the substrate 60 in the form of a strip carrying a plurality of dosage forms 45 is passed along a die 70 including at least two plates 75 each containing an aperture 80, such apertures 80 are axially aligned. The aperture(s) 80 is/are sized to permit a dosage form 45 to pass therethrough.

As the dosage form 45 on the substrate 60 strip moving past the aperture(s) 80 becomes axially-aligned with the aperture (s) 80, a pusher 85 is moved toward the aperture(s) 80 in a direction generally perpendicular to the plane of the plate 75 such that the pusher 85 contacts the substrate 60, forcing the substrate 60 against the die 70 to cut the substrate 60. In this method, the substrate 60 is cut to the size of the aperture 80, which is sized to accommodate the dosage form 45, leaving a substrate portion 90 attached to the dosage form 45. In this method, the pusher 85 may be moved to, through, or partially through the aperture(s) 80, forcing the strip to be cut by the aperture(s) 80, thus leaving an individual dosage form 45 and its attached substrate portion 90.

In a different aspect of the present invention, the pusher 85 may be replaced with a tampon body 34, thus causing the substrate 60 including the individual dosage form 45 to be cut by the aperture(s) 80 as the tampon body 34 is advanced. By employing appropriate means described below, the act of moving the tampon body 34 against the substrate 60 and toward the aperture(s) 80 can, in addition to cutting the substrate 60, result in the dosage form 45 and its associated substrate portion 90 becoming coupled to the tampon body 34. The tampon body 34 may be moved through or at least partially through the aperture(s) 80 by any suitable force, including air pressure.

In addition, the tampon body 34 may be moved through the aperture(s) 80 at least partially into a first member 14. In doing so, the cut dosage form 45 may be captured within the first member 14 adjacent the tampon body 34. In any of these cases, the process of feeding a strip of substrate 60 carrying dosage forms 45 may be a part of a larger process of manufacturing a tampon, or may be done on a separate line.

In a different aspect of the present invention, the substrate 60 may be cut so as to leave a substrate portion 90 larger than the dosage form 45. The substrate portion 90 left in this method may be circular, strip-shaped, or any other suitable arrangement or size. In this method, the substrate portion 90 will cover more of the tampon body 34 as shown in FIG. 4 when the dosage form 45 and substrate portion 90 are coupled to the tampon body 34. In a different aspect of the present invention, any suitable method of removing the dosage form 45 and a substrate portion 90 from the strip of substrate 60 may be employed. In a different aspect of the present invention, the substrate 60 may be manufactured from a material suitable for sealing a dosage form 45 in a first member 14 or other device. In various aspects of the present invention, the substrate portion 90 may remain with the dosage form 45, or the substrate portion 90 may be separated from the dosage form 45 and discarded In a different aspect of the present invention, the tampon body 34 or the pusher 85 may be advanced against a side of the substrate 60 opposite the side on which the dosage form 45 is resident with enough forced to break through the substrate 60 to push the dosage form 45 away from the substrate 60. In another aspect of the present invention, the pusher 85 may be advanced against a side of the substrate 60 opposite the side on which the dosage form 45 is positioned such that the dosage form 45 contacts and engages with a tampon body 34. In this aspect of the present invention, because the dosage form will exhibit a higher affinity for engaging the tampon body 34 than the substrate 60, the dosage form 45 will remain with the tampon body 34 once pressure from the pusher 85 is released.

Once the individual dosage forms 45 are separated from the substrate 60, a dosage form 45 may then be coupled to a tampon body 34 by any method described herein. In a first case, the dosage form 45 may be coupled to the tampon body without the substrate portion 90. In a second case, the substrate portion 90 may remain with the dosage form 45.

For the first case, in one method of coupling the dosage form 45 to the tampon body 34, a portion of the dosage form 45 is heated to melt all or some of that portion of the dosage form 45. Such heating may be accomplished using heated air, heated liquid, infrared, or any other suitable heating means. The dosage form 45 is then abutted with the tampon body 34 such that the melted region of the portion is applied with appropriate pressure to engage the tampon body 34. The melted region of the portion then re-solidifies, becoming attached to the tampon body 34. In one aspect of the present invention, the dosage form 45 is thereby mechanically engaged with the fibers of the tampon body 34. In a different aspect of the present invention, the tampon body 34 may be heated and then put in contact with the dosage form 45, thus using the heat from the tampon body 34 to heat and melt at least part of the dosage form 45.

In a different aspect of assembly for the first case, the dosage form 45 is at least partially coated with a suitable biologically-compatible adhesive such as HPMC or other suitable adhesive and then abutted with the tampon body 34 such that the dosage form 45 is affixed to the tampon body 34. The HPMC may be applied alternatively or additionally to one of the tampon body 34 or the dosage form 45.

In a different aspect of the present invention, usable in either case, the attachment may be accomplished in a manufacturing environment by introducing a small amount of heated, melted excipient such as SUPPOCIRE suppository base or other semi-synthetic glyceride onto the tampon body 34 just prior to introducing the dosage form 45 onto the tampon body 34. The heat contained in the melted excipient partially melts the dosage form 45 and creates a secure bond when both the dosage form 45 and the introduced excipient cool and harden. The heated excipient may be applied alternatively or additionally to one of the substrate portion 90 or the dosage form 45.

A tampon body 34 with a fiber structure that is less dense could absorb some or all of heated liquid excipient applied or produced in the process of coupling the dosage form 45 to the tampon body 34. In use at body temperature, the excipient may also melt and might tend to absorb further into the tampon body 34 instead of desirably migrating to the vaginal or other epithelium. For such tampons and for the second case, the substrate portion 90 may be used between the dosage form 45 and the tampon body 34. One of the primary purposes of the substrate portion 90 once it is being added to the medicated tampon assembly 10 is to inhibit any of the dosage form 45 from absorbing into the tampon body 34 during manufacture. A second primary purpose of the substrate portion 90 is to remain at least partially intact longer than the dosage form 45 when in use, thus significantly inhibiting the dosage form 45 from absorbing into the tampon body 34 during use.

Both purposes are accomplished by providing a substrate 60 with properties differentiated from the properties of the dosage form 45. For example, the substrate 60 and the dosage form 45 may be formed from similar or dissimilar materials as long as the substrate 60 has a higher melting point than the dosage form 45. In another example, the substrate 60 and the dosage form 45 may be formed from similar or dissimilar materials as long as the substrate 60 has a lower solubility than the dosage form 45. In another example, the substrate 60 and the dosage form 45 may be formed from similar or dissimilar materials as long as the substrate 60 has a lower chemical reactivity than the dosage form 45. The properties may also be mixed; a dosage form 45 that undergoes a primary structural change through melting may be combined with a substrate 60 that undergoes a primary structural change through dissolution, as long as the substrate 60 generally lasts longer in use than the dosage form 45.

In a specific example, the dosage form 45 is produced primarily from excipient that melts at human body temperature (about 37° C.±). The substrate 60 is produced primarily from excipient that melts at a higher temperature (e.g., 42-45° C.). Such a structure would inhibit migration of the therapeutic agent into the tampon body 22 during use because the excipient in the dosage form 45 carrying the therapeutic agent melts more quickly than the excipient in the substrate portion 90, which is positioned between the dosage form 45 and the tampon body 34. In other words, the excipients are selected such that the substrate 60 has a heat of fusion greater than the heat of fusion of the dosage form 45. The same effect is found when using a dosage form 45 and a substrate 60 of differentiated properties, such as different rates of solubility or chemical reactivity.

In a different aspect of assembly for the second case, the substrate portion 90 is at least partially coated with a suitable biologically-compatible adhesive such as HPMC or other suitable adhesive and then abutted with the tampon body 34 such that the dosage form 45 is affixed to the tampon body 34. The HPMC may be applied alternatively or additionally to one of the tampon body 34 or the substrate portion 90.

In a different aspect of assembly shown in FIG. 6, an applicator first member 14 is positioned in a mold or holder 95. A dosage form 45 with a substrate portion 90, preferably one in which the substrate portion 90 is larger than the dosage form 45, is positioned at the receiving end 30 of the first member 14, with the dosage form 45 positioned toward the first member 14 (see FIG. 6*a*). A tampon body 34 and optionally a second member 18 are aligned with the first member 14 and are moved into the first member 14, thus pushing the dosage form 45 with substrate portion 90 into the first member 14 (see FIG. 6*b*) at the distal end 38 of the tampon body 34 (see FIG. 6*c*). Alternatively, the mold 95 may be heated such that the dosage form 45 at least partially melts and conforms to the insertion tip 26 of the first member 14 (see FIG. 6*d*).

In a different aspect of the present invention, if the substrate 60 is a paper product or other durable and semi-durable material, then the substrate portion 90 will need to be removed from the dosage form 45 prior to coupling the dosage form 45 to the tampon body 34. In such case, the dosage form 45 may be coupled to the tampon body 34 by any of the methods described herein.

In use, and referring to FIG. 2, the medicated tampon assembly 10 functions because the second member 18 is telescopically movable relative to the first member 14. The user may position one or more fingers on the fingergrip ring 28 and one or more fingers on the finger flange 32. The user then squeezes the fingergrip ring 28 and pushes the finger flange 32 toward the fingergrip ring 28 to force the second member 18 further into the first member 14 until the dosage form 45 is expelled from the first member 14. More specifically, as the second member 18 is pushed into the first member 14, the tampon 20 is forced forward against the petals 27. The contact by the tampon 20 causes the petals 27 to radially open to a diameter that is sufficient to allow the tampon 20 to be expelled from the first member 14. With the tampon 20 properly positioned in the vaginal or other cavity, the medicated tampon assembly 10 is withdrawn and properly discarded.

Once the tampon 20 is properly positioned in the vaginal or other cavity, the tampon body 34 absorbs menses and other bodily fluids, and the dosage form 45 delivers the therapeutic agent to the vaginal or other epithelium for local or topical therapeutic action or from there, the therapeutic agent may be transferred to the uterus by normal bodily functions to relieve the condition to be treated.

The invention has been described with reference to various specific and illustrative aspects and techniques. However, it should be understood that many variations and modifications may be made while remaining within the spirit and scope of the invention.

Accordingly, this invention is intended to embrace all such alternatives, modifications and variations that fall within the spirit and scope of the appended claims.

We claim:

1. A medicated tampon comprising:
   a tampon body;
   an at least partially dissolvable or meltable planar substrate including a dosage form comprising a probiotic agent and an antifungal agent;
   wherein the dosage form is combined with the tampon body.

2. The medicated tampon of claim 1 wherein the dosage form further comprises a botanical agent.

3. The medicated tampon of claim 1 wherein the dosage form is attached to a substrate comprising a film identical to the material of the dosage form.

4. The medicated tampon of claim 1 wherein the dosage form is attached to a substrate comprising a dissolvable film comprising poly-vinyl alcohol, pectin, gelatin, HPMC or combinations thereof.

5. The medicated tampon of claim 1 wherein the dosage form comprises a gel.

6. The medicated tampon of claim 1 wherein the dosage form comprises a coating.

7. The medicated tampon of claim 1 wherein the dosage form comprises a film.

8. The medicated tampon of claim 1 wherein the tampon has a distal end and a proximal end, and the dosage form is positioned therebetween.

9. A method of manufacturing a medicated tampon comprising:
   manufacturing a tampon body;
   forming an at least partially dissolvable or meltable planar substrate separate from the tampon body, the substrate including a therapeutic agent; and
   combining the substrate with the tampon body,
   wherein the therapeutic agent comprises a probiotic agent, an antifungal agent or a combination thereof.

10. The method of claim 9 wherein a dosage form including the therapeutic agent is applied to the substrate.

11. The method of claim 9 wherein the substrate comprises a chemically reactive planar material.

12. The method of claim 10 wherein the substrate comprises a film comprising a material that is identical to the material dosage form, yet has properties that are differentiated from the properties of the dosage form.

13. The method of claim 10 wherein the substrate is formed with dimples, pockets or recesses to which the dosage form is applied.

14. The method of claim 13 wherein the substrate is rolled.

15. The method of claim 13 wherein a plurality of substrates are stacked.

16. The method of claim 10 wherein the dosage form is applied to the substrate by printing.

17. The method of claim 9 wherein the tampon body comprises an absorbent material formed from fibers that are assembled into a ribbon.

18. The method of claim 9 wherein the tampon body comprises an absorbent material formed from fibers that are assembled into a sheet.

19. The method of claim 10 wherein the dosage form comprises an excipient that melts at human body temperature.

20. The method of claim 19 wherein the dosage form is in the form of a film.

* * * * *